US006740786B1

(12) United States Patent
Jong et al.

(10) Patent No.: US 6,740,786 B1
(45) Date of Patent: May 25, 2004

(54) METHOD FOR THE PREPARATION OF 2, 2, 3, 4, 4, 4-HEXAFLUORO-1-BUTANOL

(75) Inventors: Shean-Jeng Jong, Tao-Yuan (TW); Wang-Tsae Guu, Tao-Yuan (TW); Chung-Mou Liang, Tao-Yuan (TW)

(73) Assignee: Chung-Shan Institute of Science & Technology, Tao-Yuan (TW)

( * ) Notice: Subject to any disclaimer, the term of this patent is extended or adjusted under 35 U.S.C. 154(b) by 38 days.

(21) Appl. No.: 10/291,398

(22) Filed: Nov. 12, 2002

(51) Int. Cl.$^7$ ............................................... C07C 31/34
(52) U.S. Cl. ....................................................... 568/842
(58) Field of Search ......................................... 568/842

(56) References Cited

U.S. PATENT DOCUMENTS 3,727,129 A * 4/1973 Hummert .................... 324/547
2003/0158452 A1 * 8/2003 Tohma et al. ................ 568/842

* cited by examiner

*Primary Examiner*—Michael L. Shippen
(74) *Attorney, Agent, or Firm*—Bacon & Thomas, PLLC

(57) ABSTRACT

The method for preparing 2,2,3,4,4,4-hexafluoro-1-butanol includes reacting methanol and hexafluoropropene in the presence of a free radical initiator such as di-isopropyl peroxydicarbonate at 25–50° C. and a pressure of 100–300 psi in an autoclave. An inert gas such as nitrogen and argon is added to the autoclave when the pressure is lower than 100 psi in the course of the reaction.

7 Claims, No Drawings

METHOD FOR THE PREPARATION OF 2, 2, 3, 4, 4, 4-HEXAFLUORO-1-BUTANOL

FIELD OF THE INVENTION

The present invention is related to a preparation method of 2,2,3,4,4,4-hexafluoro-1-butanol, and in particular to a low temperature and high pressure method for the preparation of 2,2,3,4,4,4-hexafluoro-1-butanol.

BACKGROUND OF THE INVENTION

Japanese patent publication Nos. 200252823 (2002), 200253506 (2002), and 200253507 (2002) describe that a short-chain fluoroalkanol having the following formula (I) can be used as a solvent for an optical information recording dye of CD-R and DVD-R:

$$H(CFR_1CF_2)_nCH_2OH \qquad (I)$$

wherein the formula (I) represents 2,2,3,3-tetrafluoro-1-propanol, when $R_1$=F, n=1; 2,2,3,3,4,4,5,5-octafluoro-1-pentanol, when $R_1$=F, n=2; and 2,2,3,4,4,4-hexafluoro-1-butanol (hereinafter abbreviated as HFB), when $R_1$=$CF_3$, n=1.

The methods for the preparation of HFB published in the literature include reacting hexafluoropropene and methanol under irradiation of light, heating and in the presence of a free radical initiator, wherein J. Fluorine Chem., 291,28 (1985) and a patent application with a publication number of CS268247 disclose a synthesis method by using irradiation of light. This method requires special lighting equipment, and suffers an abrupt change in temperature or pressure during the reaction. Therefore, this method is not easy to be put into mass production.

U.S. Pat. No. 3,927,129 (1975) discloses a high-temperature synthesis method, wherein hexafluoropropene and methanol are reacted at 280° C. for four days, and the yield is 85%. The yield drops to 31%, when the reaction temperature is 240° C. The high temperature and long reaction time are adverse factors for a mass production based on this synthesis method.

PCT application WO 01/02329 (2001) discloses a process for producing fluoroalkanol including heating methanol in an autoclave at a temperature of 125° C., separately and continuously adding hexafluoropropene and a free radical initiator of di-t-butyl peroxide in methanol to the autoclave. A high-pressure feeding apparatus is required for the additions of hexafluoropropene and the free radical initiator. Moreover, the rates of the additions must be controlled accurately to avoid dangers caused by an abrupt increase in temperature or pressure in the autoclave. For an one-liter autoclave only 125 g of hexafluoropropene was reacted per batch.

PCT application WO 01/62694 (2001) discloses a process for preparation of HFB including heating methanol, a free radical initiator and a small amount of hexafluoropropene in an autoclave, and feeding hexafluoropropene during the reaction. This process also requires high-pressure feeding apparatus, and suffers a continuous increase in reaction temperature. In Example 1 of this PCT application, the reaction temperature was increased from the starting 48° C. to 75° C. after 7-hour of hexafluoropropene feeding, wherein t-butylperoxy-2-ethyl hexanoate was used as a free radical initiator and an 1-L autoclave was used. A similar trend of reaction temperature increase was also observed in the other examples. Therefore, the rates of the hexafluoropropene feeding must be controlled accurately to avoid dangers caused by an abrupt increase in temperature or pressure in the autoclave. For the one-liter autoclave used in Example 1 of this prior art 277 g of hexafluoropropene was reacted per batch, and 5510 g of hexafluoropropene was reacted per batch for a 20-L autoclave used in Example 2. The product yield after distillation was about 75%.

SUMMARY OF THE INVENTION

The present invention provides a method for preparing 2,2,3,4,4,4-hexafluoro-1-butanol comprising reacting methanol and hexafluoropropene in the presence of a free radical initiator such as di-isopropyl peroxydicarbonate at 25–50° C., preferably 40–50° C., and a pressure of 100–300 psi in an autoclave for a period of time. An inert gas such as nitrogen and argon is added to the autoclave when the pressure is lower than 100 psi in the course of the reaction.

In the method of the present invention, preferably nitrogen is introduced to the autoclave so that the pressure is maintained at 200–300 psi.

In the method of the present invention, preferably methanol and hexafluoropropene is reacted with a molar ratio of hexafluoropropene to methanol of 0.2–1 at the beginning of the reaction, and no hexafluoropropene being added in the course of the reaction. More preferably, molar ratio of hexafluoropropene to methanol is of 0.3–0.4.

Preferably, said period of time for said reaction is 20–40 hours.

DETAILED DESCRIPTION OF PREFERRED EMBODIMENTS

The present invention discloses a novel method for preparing 2,2,3,4,4,4-hexafluoro-1-butanol (HFB) by reacting methanol and hexafluoropropene in the presence of a free radical initiator at 25–50° C. in an autoclave, wherein an insert gas including (but not limited to) nitrogen and argon may be added to the autoclave to maintain a pressure in the autoclave not lower than a predetermined value. The advantages of the present invention include: no addition of reactants during the reaction, no abrupt change in temperature, and increase in the amount of reactants reacted per volume of the autoclave per batch.

An example of the free radical initiator used in the method of the present invention is di-isopropyl peroxydicarbonate. The amount of the free radical initiator used ranges from 0.001 to 10, and preferably from 0.01 to 0.06, times of the weight of methanol used.

The present invention can be better understood by the following examples which are illustrative only, not for limiting the scope of the present invention.

EXAMPLE 1

To a mixture of 240 g of methanol and 3 g of a free radical initiator, Luperox IPP, sold by ELF Atochem, Inc. (containing 27–28% of di-isopropyl peroxydicarbonate) in a 600-ml autoclave, 370 g of hexafluoropropene was added after degas thereof. Nitrogen was then introduced to the autoclave until the pressure therein reached 263 psi. The mixture in the autoclave was heated to 50° C. in 10 minutes, and the pressure was increased slowly to 287 psi right after the heating. The temperature was maintained at 50° C. for reaction for 24 hours by heating. During the reaction nitrogen was supplied to the autoclave when the pressure therein dropped below 250 psi, and the nitrogen supply was cut off when it was back up to 300 psi. The reaction mixture was removed from the autoclave after the reaction, and distilled. The distilled product collected at 114–118° C. is 90 g.

EXAMPLE 2

To a mixture of 240 g of methanol and 4 g of Luperox IPP in a 600-ml autoclave, 370 g of hexafluoropropene was added after degas thereof. Nitrogen was then introduced to the autoclave until the pressure therein reached 290 psi. The mixture in the autoclave was heated to 50° C. in 10 minutes, and the pressure was decreased to 285 psi right after the heating. The temperature was maintained at 50° C. for reaction for 24 hours by heating. During the reaction nitrogen was supplied to the autoclave when the pressure therein dropped below 250 psi, and the nitrogen supply was cut off when it was back up to 300 psi. The reaction mixture was removed from the autoclave after the reaction, and distilled. The distilled product collected at 114–118° C. is 100 g.

EXAMPLE 3

To a mixture of 240 g of methanol and 10 g of Luperox IPP in a 600-ml autoclave, 368 g of hexafluoropropene was added after degas thereof. Nitrogen was then introduced to the autoclave until the pressure therein reached 290 psi. The mixture in the autoclave was heated to 40° C. in 4 minutes, and the pressure was decreased to 229 psi right after the heating. The temperature was maintained at 40° C. for reaction for 8 hours by heating; then increased to 45° C. by heating in 20 minutes, and maintained at 45° C. for reaction for 18 hours by heating; and finally increased to 50° C. by heating in 20 minutes, and maintained at 50° C. for reaction for 10 hours by heating. During the reaction nitrogen was supplied to the autoclave when the pressure therein dropped below 220 psi, and the nitrogen supply was cut off when it was back up to 300 psi. The reaction mixture was removed from the autoclave after the reaction, and distilled. The distilled product collected at 114–118° C. is 300 g. Yield 67%.

EXAMPLE 4

To a mixture of 240 g of methanol and 10 g of Luperox IPP in a 600-ml autoclave, 360 g of hexafluoropropene was added after degas thereof. The pressure in the autoclave at room temperature (25° C.) was 123 psi. The mixture in the autoclave was heated to 50° C. in 40 minutes, and the pressure was increased to 203 psi right after the heating. The temperature was maintained at 50° C. for reaction for 36 hours by heating. After the reaction the pressure in the autoclave dropped to 94 psi. The reaction mixture was removed from the autoclave after the reaction, and distilled. The distilled product collected at 114–118° C. is 255 g.

EXAMPLE 5

To a mixture of 240 g of methanol and 10 g of Luperox IPP in a 600-ml autoclave, 290 g of hexafluoropropene was added after degas thereof. Nitrogen was then introduced to the autoclave until the pressure therein reached 296 psi. The mixture in the autoclave was heated to 40° C. in 18 minutes, and the pressure was decreased slowly to 259 psi right after the heating. The temperature was maintained at 40° C. for reaction for 22 hours by heating. During the reaction nitrogen was supplied to the autoclave when the pressure therein dropped below 230 psi, and the nitrogen supply was cut off when it was back up to 300 psi. The reaction mixture was removed from the autoclave after the reaction, and distilled. The distilled product collected at 114–118° C. is 30 g.

CONTROL EXAMPLE 1

To a mixture of 240 g of methanol and 15 g of Luperox IPP in a 600-ml autoclave, 366 g of hexafluoropropene was added after degas thereof. Nitrogen was then introduced to the autoclave until the pressure therein reached 275 psi. The mixture in the autoclave was heated to 40° C. in 10 minutes, and the pressure was decreased to 243 psi right after the heating. The temperature was maintained at 40° C. for reaction for 4 hours by heating, then was increased to 60° C. in 10 minutes (pressure ramped from 250 psi to 630 psi), and maintained at 60° C. for 17 hours (pressure dropped finally to 271 psi). The reaction mixture was removed from the autoclave after the reaction, and distilled. The distilled product collected at 114–118° C. is 264 g.

CONTROL EXAMPLE 2

To a mixture of 240 g of methanol and 3 g of Luperox IPP in a 600-ml autoclave, 364 g of hexafluoropropene was added after degas thereof. Nitrogen was then introduced to the autoclave until the pressure therein reached 297 psi. The mixture in the autoclave was heated slowly to 100° C. in 10 minutes, wherein the pressure was increased to 990 psi when the temperature reached 75° C., and was 886 psi when the temperature reached 1000° C. The temperature was maintained at 100° C. for reaction for 26 hours by heating (pressure decreased from 886 psi to 481 psi). The reaction mixture was removed from the autoclave after the reaction, and distilled. The distilled product collected at 114–118° C. is 106 g.

The results are listed in Table 1. It can be from the results of Example 1 and Control Example 2 that the yield is not enhanced by increasing the reaction temperature high than 50° C., instead the pressure in the autoclave is abruptly increased. Control Example 2 shows that the pressure in the autoclave ramps as the reaction temperature is raised to higher than 50° C. during the reaction, even though the initial reaction temperature is lower than 50° C. The results of Examples 3 and 4 indicate that the nitrogen supply for maintaining the reaction pressure can enhance the yield. It is believed that the low yield of Example 3 is due to a low reaction temperature.

TABLE 1

| | IPP, g | $CH_3OH$, g (mole) | $CF_3CF=CF_2$ (mole) | Reaction time (hour) | Weight of product, g (yield, %) |
|---|---|---|---|---|---|
| Example 1 | 3 | 240 (7.5) | 370 (2.47) | 24 | 90 |
| Example 2 | 4 | 240 (7.5) | 370 (2.47) | 24 | 100 |
| Example 3 | 10 | 240 (7.5) | 368 (2.45) | 36 | 300 (67%) |
| Example 4 | 10 | 240 (7.5) | 360 (2.40) | 36 | 255 |
| Example 5 | 10 | 240 (7.5) | 290 (1.93) | 22 | 30 |
| Control Ex. 1 | 15 | 240 (7.5) | 366 (2.44) | 21 | 264 |
| Control Ex. 2 | 3 | 240 (7.5) | 364 (2.43) | 26 | 106 |

What is claimed is:

1. A method for preparing 2,2,3,4,4,4-hexafluoro-1-butanol comprising reacting methanol and hexafluoropropene in the presence of a free radical initiator s at 25–50° C., and a pressure of 100–300 psi in an autoclave for a period of time, wherein an inert gas is added to the autoclave when said pressure is lower than 100 psi in the course of the reaction.

2. The method according to claim 1, wherein nitrogen is introduced to the autoclave so that said pressure is maintained at 200–300 psi.

3. The method according to claim 1, wherein said free radical initiator is di-isopropyl peroxydicarbonate.

4. The method according to claim 1, wherein methanol and hexafluoropropene is reacted with a molar ratio of hexafluoropropene to methanol of 0.2–1 at the beginning of the reaction, and no hexafluoropropene being added in the course of the reaction.

5. The method according to claim 4, wherein said molar ratio of hexafluoropropene to methanol is of 0.3–0.4.

6. The method according to claim 4, wherein said period of time is 20–40 hours.

7. The method according to claim 3, wherein said reaction temperature is 40–50° C.

* * * * *